United States Patent [19]

Tominaga

[11] Patent Number: 4,924,810
[45] Date of Patent: May 15, 1990

[54] INSECT KEEPING AND OBSERVING CONTAINER

[75] Inventor: Kazutoshi Tominaga, Osaka, Japan

[73] Assignee: Kabushiki Kaisha Tominaga Jyushi Kogyosho, Osaka, Japan

[21] Appl. No.: 376,399

[22] Filed: Jul. 6, 1989

[51] Int. Cl.⁵ .............................. A01K 1/00
[52] U.S. Cl. ................................. 119/15
[58] Field of Search ................ 119/15, 17, 1

[56] References Cited

U.S. PATENT DOCUMENTS

| | | | |
|---|---|---|---|
| 3,687,110 | 8/1972 | Braunhut | 119/15 |
| 3,742,908 | 7/1973 | Merino | 119/15 |
| 3,789,799 | 2/1974 | Orfei | 119/15 |
| 3,865,082 | 2/1975 | Lovitz et al. | 119/15 |
| 3,958,534 | 5/1976 | Perkins et al. | 119/15 |
| 4,723,512 | 2/1988 | Margolis | 119/15 |

Primary Examiner—John Weiss
Attorney, Agent, or Firm—Collard, Roe & Gangano

[57] ABSTRACT

An insect keeping and observing container comprises a round recessed part in the center of a removable lid of a main transparent container and a round plate at the bottom of the recessed part which can be removed by cutting joint pieces at the annular edge outside the round plate. Accordingly, the insect keeping and observing container can be connected to tubular members which serve as a tunnel alley to a rodent's breeding housing by removing the round plate.

4 Claims, 3 Drawing Sheets

INSECT KEEPING AND OBSERVING CONTAINER

BACKGROUND OF THE INVENTION

1. Field of the invention

The present invention relates to a container or a cage used for keeping and observing mainly insects (like beetles, bell-ring insects etc.)

2. Description of the Prior Art

A transparent container made of synthetic resin with a lid is used for confining and carrying insects or for keeping and observing insects at home for a short period.

The container consists of a lower main containing part made of transparent synthetic resin and an upper removable lid fixed firmly on the main part so as not to open easily, and in most cases the lid has a handle for carrying.

These containers for keeping and observing insects are generally left empty after being used temporarily or for a short period.

On the other hand, nowadays, rodents such as hamsters are kept by many animal-loving families.

In order to keep these rodents in a favorable condition, it is necessary to give them a housing simulating a natural environment and permitting them to exercise freely. For the purpose of meeting the above-mentioned requirement, as seen in the U. S. Pat. No. 3,742,908, many detached housings are connected to a main housing. For example, eating, climbing up, excreting waste material, etc. are done in the detached housings.

When these backgrounds are taken into consideration, the insect keeping and observing container has a suitable size in a usage of the said detached housing.

The conventional insect keeping and observing containers however, didn't have joints to pass through the tubular members and remained useless in the above-mentioned usage.

SUMMARY OF THE INVENTION

It is an object of the present invention to provide a container which can be used as a component material of a breeding house for rodents (such as hamsters) after it was used for keeping and observing insects.

Another object of the present invention is to supply an insect keeping and observing container to which tubular members connecting to a central housing for rodents are easily joinable when it is necessary.

The other object of the present invention is to provide a container whose opening part to connect the tubular members is obviated any possibility of captured insects' escape when it is used in its original usage of keeping insects.

In order to attain these objects, the present invention relates to an insect keeping and observing container characterized by a structure which is shown as follows: the container is composed of a lower box-shaped transparent main container and its removable lid firmly fixed on the main container, and the lid has a round recessed part in the upper center. The recessed part consists of a circumference wall protruding inside the lid, a round plate kept in a separatable position with several slits in its circumference edge, and several breakable joint supporting pieces which connect the said round plate to the edge of the said circumference wall.

Accordingly, when the above-mentioned container is used as a detached housing for rodents such as hamsters, the recessed part can be opened by cutting the joint supporting pieces with a knife and removing the round bottom plate. Then it is possible to pass a tubular member for hamsters' tunnel alley through the recessed part and support it firmly making use of the circumference wall.

DESCRIPTION OF THE PREFERRED EMBODIMENTS

Figure 1:
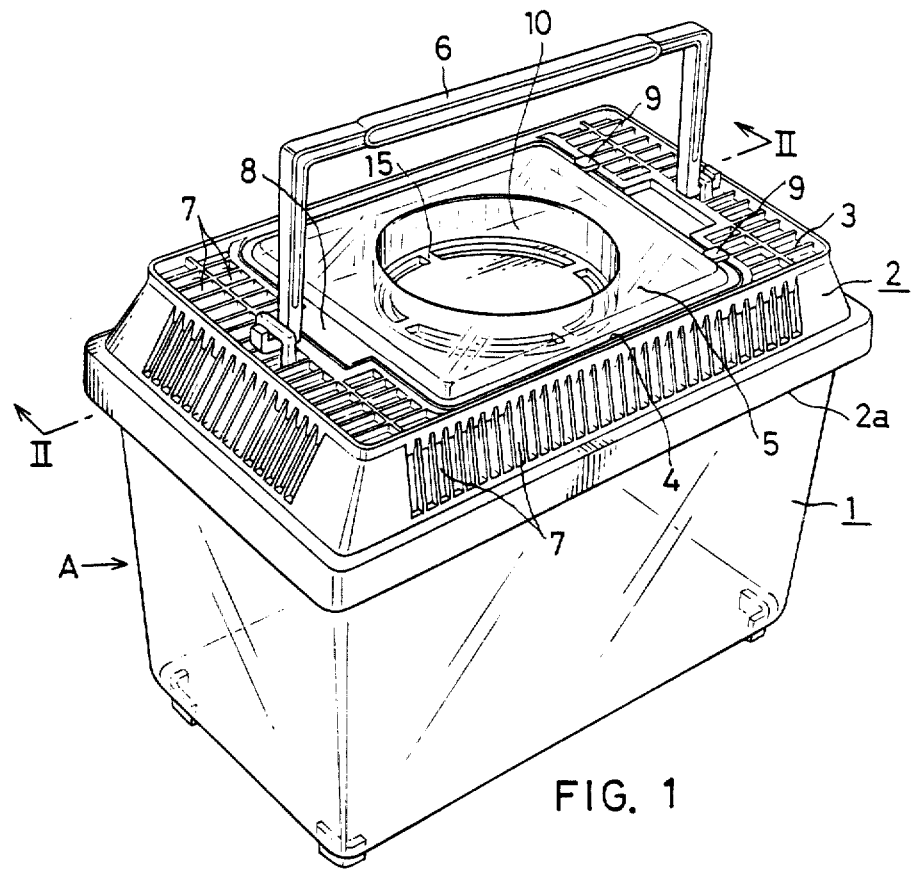
FIG. 1 illustrates a perspective view of the insect keeping and observing container according to the present invention.
Figure 2:
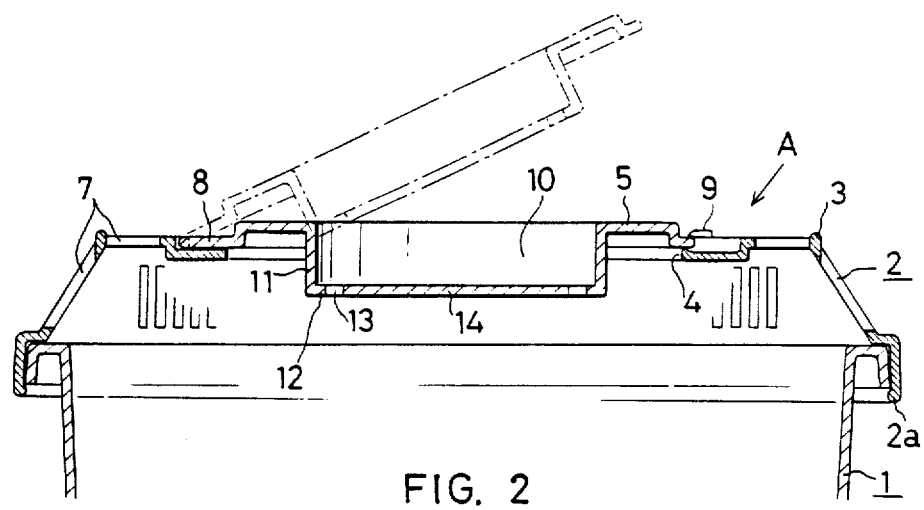
FIG. 2 illustrates a cross-sectional view of the upper part of the container taken along the line II—II in FIG. 1.

As is shown in FIG. 1 or FIG. 2, an insect keeping and observing container or a cage (A) consists of a main container, a lower part of the system and a lid (2), an upper part of it. The main container (1) is made of transparent resin such as polystyrene resin product, and shaped in a structure of a rectangular box with its walls widened gradually to the top.

On the other hand, the lid (2) is attached to the opening of the main container (1) in press-fit relation with its fringe (2a) fitted to the opening. The lid (2) comprises a main part (3) forming a base, a closable opening (5) covering an in and out opening (4) for insects in the center of the said main part (3) and a handle member (6) which is placed spanning over the said closable opening (5) on the said main part (3). The main part is made of synthetic resin mold (such as polypropylene) and has a lot of air blow slits (7).

The closable opening (5) placed in the center on the lid (2) is made of transparent synthetic resin such as polystyrene resin product and its fixed member (8) of one side is anchored in the main part (3), so that it can be turned and opened. Furthermore, the other side of it is hooked by a small stopper (9) protruding from the main part (3), when it is closed, preventing it from accidental opening by using the stopper's resiliency. Taking out and putting in of insects are performed by opening the closable opening (5).

In the center of the closable opening (5), there is installed a round recessed part (10) whose inside diameter is 58 mm for example and whose depth is from 10–20 mm, more favorably 15 mm. In the bottom surface of the recessed part, there are provided slits (13) forming an annular shape close to the peripheral fringe, separating a round plate (14) from the said fringe part (12) slightly protruding from the lower edge of the circumference wall (11). Accordingly, the fringe part (12) and the round plate (14) are partially connected each other by joint pieces (15), so the bottom surface of the recessed part (10) is covered with the round plate obviating any possibility of captured insects escape.

The recessed part (10) possesses no peculiar necessity when the container (A) is used as an insect cage an original means to keep and observe insects. The said recessed part (10) executes its usefulness when the container (A) is used as a housing member for breeding hamsters.

Figure 4:
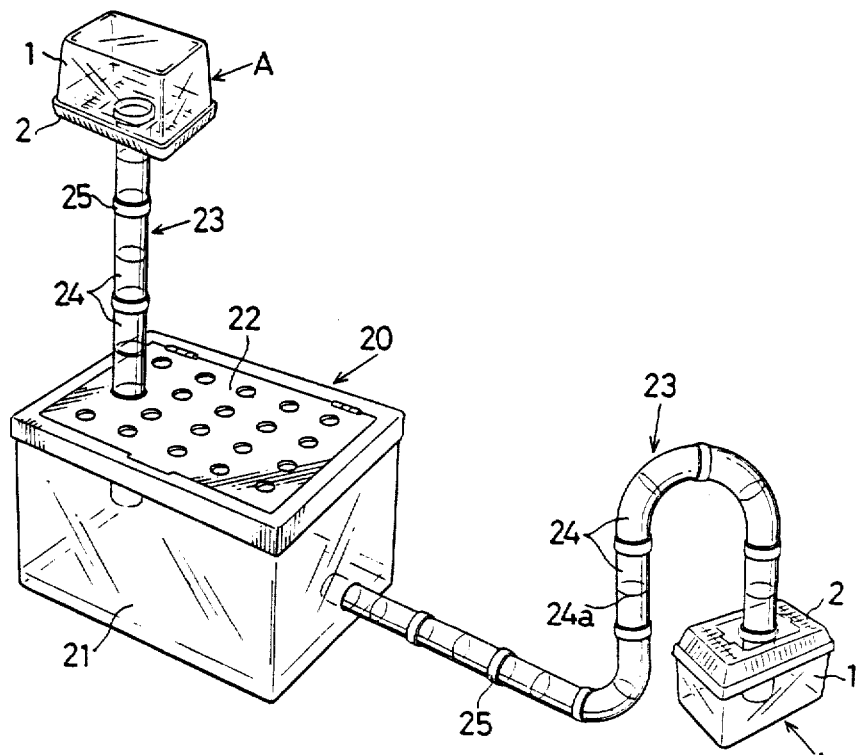
FIG. 4 illustrates a perspective view of an exampled composition of the container when it is used as a detached housing for a rodent breeding habitat.
Figure 5:
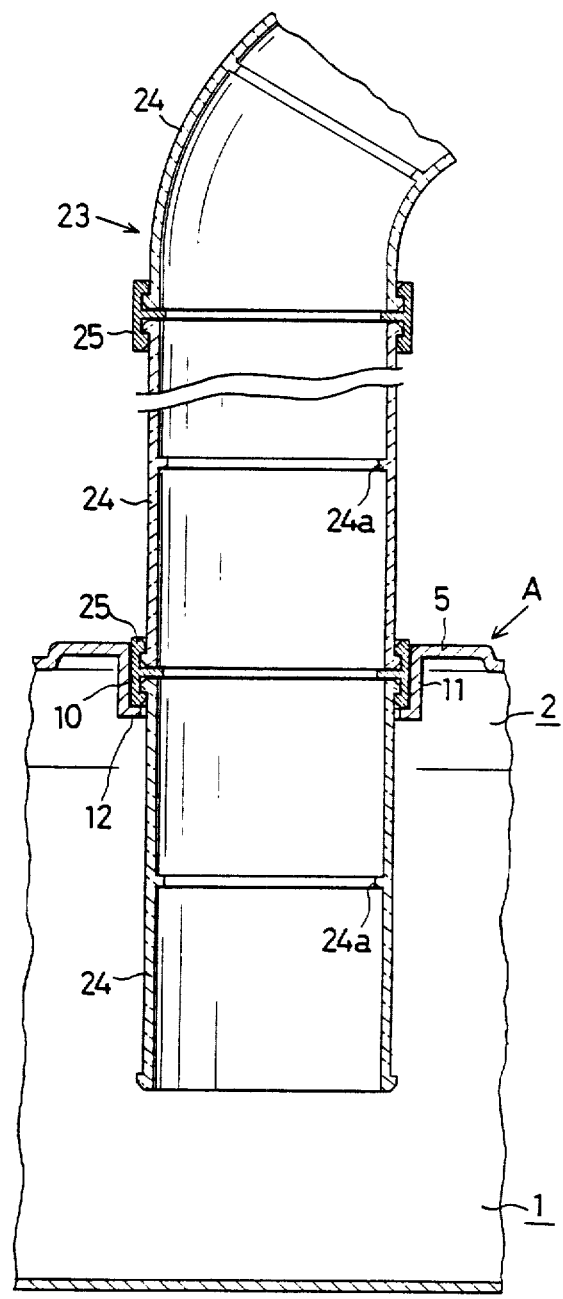
FIG. 5 illustrates an elevational cross-sectional view of the joint part showing the condition wherein a tubular member is passed through when the disclosed container is attached to the housing composition shown in FIG. 4.

FIG. 4 as well as FIG. 5 shows an example of the structure wherein container (A) is used as a breeding house for rodents such as hamsters.

In the example of the housing structure illustrated in FIG. 4, a main housing or a cage (20) forming a basic habitat for example hamsters, is bigger in size than that of container (A) and comprises a transparent main container (21) covered with a lid (22) having air intake holes. One end of tubular member (24) are connected to the main housing (20) in order to provide one or more tunnel alleys (23) for the animal to come out or exercise.

The tubular members (24) are made of transparent synthetic resin with a certain length and a favorable length of the tunnel alley can be obtained by connecting some of them using joint members (25). Inside the tubular member there is made a circular step (24a) for a hamster to put the legs on and walk in the slanting way or climb up or down the vertical tunnel safely (Ref. FIG. 5).

Figure 3:
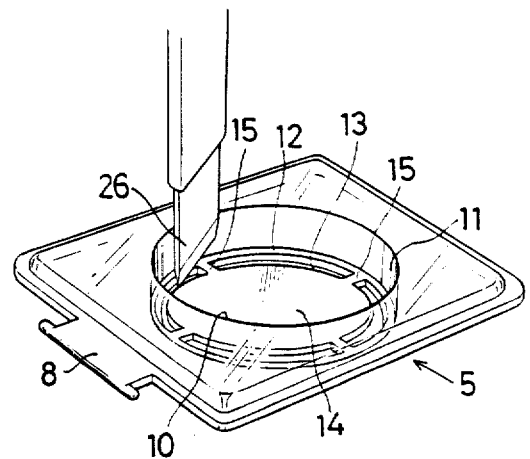
FIG. 3 illustrates a perspective view of the lid part.

To the end of the tunnel alley (23) there is connected the disclosed container (A), providing a hamster a confining space to eat, play, view the surroundings or excrete waste material inside. When this tubular member (24) is connected, the recessed part (10) of the container's (A) lid (2) can be opened at its bottom by removing its round plate (14). The removal of the round plate (14) is performed by cutting the joint pieces (15) off with an optional cutting tool (26) (a knife) as is shown FIG. 3. When the round plate (14) was removed in this way, there remains the annular fringe (12) inside of the bottom of the recessed part (10). Accordingly, as is shown in FIG. 5, the joint member (25) is inserted into the recessed part (10) being supported on the fringe part (12) and then the tubular members are associated with each other from both sides of the said joint member (25) in press-fit relation, forming the tunnel alley (23) from outside through the container (A).

Displaying of the container (A) comprises two ways: In one way, the container (A) is placed on the top of the vertical tunnel alley (23), being connected upside down shown in the upper of FIG. 4, and in the other way, it is connected to the main housing (20) in a normal way on the floor.

In the container (A), animal toys (a wheel etc.) or a feeding container can be placed, if necessary.

As is shown in the above, the disclosed insect keeping and observing container can provide an advantageous way of usage as a housing member of a habitat for rodents such as hamsters when it is not used in its original usage.

What is claimed is:

1. An insect keeping and observing container; comprises a transparent main container, a removable lid covering said container, a round recessed part in the center of the upper side of said lid, a fringe part protruding inside from the lower edge of a circumference wall of said recessed part, a round plate inside said fringe part which is separated from the said fringe part by annular slits, and several breakable joint pieces which partially connect said round plate to said fringe part at several annular positions.

2. An insect keeping and observing container as claimed in claim 1, wherein a closable opening is installed in the center of said lid, wherein said recessed part is formed 3. An insect keeping and observing container as claimed ed in claim 2, wherein the said closable opening is made of transparent material.

4. An insect keeping and observing container as claimed in claim 1, wherein the depth of said recessed part is from 10 to 20 mm.

* * * * *